(12) United States Patent
Siegert et al.

(10) Patent No.: US 9,365,844 B2
(45) Date of Patent: *Jun. 14, 2016

(54) PERFORMANCE-ENHANCED PROTEASE VARIANT

(75) Inventors: Petra Siegert, Haan (DE); Ulrich Schwaneberg, Kelmis-Hergenrath (BE); Ronny Martinez, Aachen (DE); Marion Merkel, Cologne (DE); Astrid Spitz, Moers (DE); Susanne Wieland, Zons Dormagen (DE); Hendrik Hellmuth, Duesseldorf (DE); Karl-Heinz Maurer, Erkrath (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 617 days.

This patent is subject to a terminal disclaimer.

(21) Appl. No.: 13/583,602

(22) PCT Filed: Mar. 10, 2011

(86) PCT No.: PCT/EP2011/053607
§ 371 (c)(1),
(2), (4) Date: Sep. 7, 2012

(87) PCT Pub. No.: WO2011/110625
PCT Pub. Date: Sep. 15, 2011

(65) Prior Publication Data
US 2013/0005637 A1  Jan. 3, 2013

(30) Foreign Application Priority Data
Mar. 11, 2010 (DE) .......................... 10 2010 002 762

(51) Int. Cl.
*C12N 9/54* (2006.01)
*C11D 3/386* (2006.01)

(52) U.S. Cl.
CPC ........ *C12N 9/54* (2013.01); *C11D 3/386* (2013.01); *C11D 3/38681* (2013.01)

(58) Field of Classification Search
None
See application file for complete search history.

(56) References Cited

U.S. PATENT DOCUMENTS 7,262,042 B2 * 8/2007 Weber et al. .................. 435/212
7,449,187 B2 * 11/2008 Weber ...................... A61K 8/66
424/184.1

FOREIGN PATENT DOCUMENTS

WO       WO03054184       *  7/2003   ............... C12N 9/54

OTHER PUBLICATIONS

Issued_Patents_AA from U.S. Pat. No. 7,262,042; Weber et al (2007) Seq Id No. 3. Alignment with Seq Id No. 1.*
Issued_Patents_AA: database Seq Id No. 3 from U.S. Pat. No. 7,449,187, Weber et al, 2008. Alignment with Seq Id No. 1 w/ I21V substitution, as herein.*

* cited by examiner

*Primary Examiner* — Sheridan Swope
(74) *Attorney, Agent, or Firm* — P. Scott Smith

(57) ABSTRACT

Proteases encompassing an amino acid sequence that is at least 70% identical to the amino acid sequence indicated in SEQ ID NO. 1 over its entire length, and exhibit the amino acid substitution I21V in the count in accordance with SEQ ID NO. 1, agents that encompass such proteases, display very good cleaning performance on protease-sensitive stains.

5 Claims, 1 Drawing Sheet

```
                          1                                                  50
SEQ ID NO. 1    (1)   QQTVPWGISRVQAPTVHNRGITGSGVKVAILDTGIAQHSDLTIRGGASFV
SEQ ID NO. 2    (1)   QQTVPWGISRVQAPTVHNRGVTGSGVKVAILDTGIAQHSDLTIRGGASFV
SEQ ID NO. 3    (1)   AQSVPWGISRVQAPAAHNRGLEGSGVKVAVLDTGISTRPDLNIRGGASFV
                         51                                                 100
SEQ ID NO. 1   (51)   PGESTTADLNGHGTHVAGTVAALNNSIGVIGVAPSADLYAVKVLGANGRG
SEQ ID NO. 2   (51)   PGESTTADLNGHGTHVAGTVAALNNSIGVIGVAPSADLYAVKVLGANGRG
SEQ ID NO. 3   (51)   PGEPSTQDGNGHGTHVAGTIAALNNSIGVLGVAPSAELYAVKVLGADGRG
                        101                                                 150
SEQ ID NO. 1  (101)   SVSGIAQGLEWAATNGMHIANMSLGSDAPSTTLEPAVNYATSRGVLVIAA
SEQ ID NO. 2  (101)   SVSGIAQGLEWAATNNMHIANMSLGSDAPSTTLEPAVNYATSRGVLVIAA
SEQ ID NO. 3  (101)   AISSIAQGLEWAGNRGMHVANLGLGSPSPSATLEQAVRSATSRGVLVVAA
                        151                                                 200
SEQ ID NO. 1  (151)   TGNNGTGSIGYPARYANAMAVGATDQNNRPASFSQYGTGIDIVAPGVGIQ
SEQ ID NO. 2  (151)   TGNNGTGSIGYPARYANAMAVGATDQNNRRASFSQYGTGIDIVAPGVGIQ
SEQ ID NO. 3  (151)   SGNSGASSISYPARYANAMAVGATDQNNNKASFSQYGAGLDIVAPGVNVQ
                        201                                                 250
SEQ ID NO. 1  (201)   STYLNNSYASMPGTSMATPHVAGVAALVKQKNPSWNATQIRNHLKNTATN
SEQ ID NO. 2  (201)   STYLNNSYASMPGTSMATPHVAGVAALVKQKNPSWNATQIRNHLKNTATN
SEQ ID NO. 3  (201)   STYPGSTYASLNGTSMATPHVAGAAALVKQKNPSWSNVQIPNHLKNTATS
                        251         269
SEQ ID NO. 1  (251)   LGNSSQFGSGLVNADAATR
SEQ ID NO. 2  (251)   LGNSSQFGSGLVNADAATR
SEQ ID NO. 3  (251)   LGSTNLYGSGLVNAEAATR
```

PERFORMANCE-ENHANCED PROTEASE VARIANT

CROSS-REFERENCE TO RELATED APPLICATIONS

This application is a U.S. National-Stage entry under 35 U.S.C. §371 based on International Application No. PCT/EP2011/053607, filed Mar. 10, 2011, which was published under PCT Article 21(2) and which claims priority to German Application No. 10 2010 002 762.6, filed Mar. 11, 2010, which are all hereby incorporated in their entirety by reference.

TECHNICAL FIELD

The technical field is in the sector of enzyme technology. The technical field relates in particular to proteases and to the manufacture thereof, whose amino acid sequence has been modified in particular in terms of use in washing and cleaning agents, to all sufficiently similar proteases having a corresponding modification, and to nucleic acids coding for them. The technical field further relates to methods and uses of these proteases and to agents, in particular washing and cleaning agents, containing them.

BACKGROUND

Proteases are among the technically most important of all enzymes. For washing and cleaning agents they are the longest-established enzymes, contained in practically all modern high-performance washing and cleaning agents. They cause the breakdown of protein-containing stains on the material to be cleaned. Among these in turn, proteases of the subtilisin type (subtilases, subtilopeptidases, EC 3.4.21.62), which are categorized among the serine proteases because of the catalytically effective amino acids, are particularly important. They act as nonspecific endopeptidases and hydrolyze any acid-amide bonds that are located within peptides or proteins. Their optimum pH is usually in the markedly alkaline range. An overview of this family is offered, for example, by the article "Subtilases: subtilisin-like proteases" by R. Siezen, in "Subtilisin enzymes" pp. 75-95, edited by R. Bott and C. Betzel, New York, 1996. Subtilases are formed naturally by microorganisms; among them, the subtilisins formed and secreted by *Bacillus* species are to be mentioned in particular as the most significant group within the subtilases.

Examples of proteases of the subtilisin type used with preference in washing and cleaning agents are the subtilisins BPN' and Carlsberg, protease PB92, subtilisins 147 and 309, the protease from *Bacillus lentus*, in particular from *Bacillus lentus* DSM 5483, subtilisin DY, and the enzymes (to be classified, however, as subtilases and no longer as subtilisins in the strict sense) thermitase, proteinase K, and the proteases TW3 and TW7, as well as variants of the aforesaid proteases that exhibit an amino acid sequence modified as compared with the initial protease. Proteases are modified, in controlled or random fashion, using methods known from the existing art, and are thereby optimized, for example, for use in washing and cleaning agents. These include point mutagenesis, deletion or insertion mutagenesis, or fusion with other proteins or protein parts. Correspondingly optimized variants are thus known for most proteases known from the existing art.

The International Patent Application WO 03/054185 discloses alkaline proteases from *Bacillus gibsonii* (DSM 14391), including for use thereof in washing or cleaning agents. This strain was deposited on Mar. 1, 2001, in accordance with the Budapest Treaty on the International Recognition of the Deposit of Microorganisms of Apr. 28, 1977, at the German Collection of Microorganisms and Cell Cultures [Deutsche Sammlung von Mikroorganismen und Zellkulturen GmbH], Inhoffenstrasse 7B, D-38124 Braunschweig under the designation ID 01-192 and entry number DSM 14391. These proteases exhibit considerable differences in amino acid sequence as compared with the proteases recited above, so that an identity comparison of the amino acid sequences yields identity values that are below 80% identity. For the alkaline proteases from *Bacillus gibsonii* (DSM 14391), only a few protease variants optimized for use in washing and cleaning agents are so far known in the existing art.

SUMMARY

At least one object herein is therefore to further develop a protease of the type of the alkaline protease from *Bacillus gibsonii* DSM 14391, resp. a protease sufficiently identical thereto (in terms of sequence identity) and to obtain protease variants that are suitable for use thereof in washing or cleaning agents, and advantageously are improved. Another object herein is to provide a method for manufacturing the protease. In addition, other objects, desirable features and characteristics will become apparent from the detailed description, and the appended claims, taken in conjunction with the accompanying drawings and the preceding background.

DESCRIPTION OF THE FIGURES

FIG. 1 is a sequence comparison (alignment) of the sequence in accordance with SEQ ID NO. 1, SEQ ID NO. 2, and SEQ ID NO. 3, prepared using the Vector NTI® Suite 10.3 Program (Invitrogen Corporation, Carlsbad, Calif.) under standard parameters.

DETAILED DESCRIPTION

In an exemplary embodiment, a protease encompassing an amino acid sequence that is at least 70% identical to the amino acid sequence indicated in SEQ ID NO. 1 over its entire length, and exhibits the amino acid substitution I21V in the count in accordance with SEQ ID NO. 1 is provided.

In another embodiment, a method for manufacturing a protease is provided. The method encompasses the introduction of an amino acid substitution I21V in the count in accordance with SEQ ID NO. 1 into an initial protease that is at least 70% identical to the amino acid sequence indicated in SEQ ID NO. 1 over its entire length.

A "protease" for purposes herein therefore encompasses both the protease as such and a protease manufactured with a method described herein. All statements with regard to the protease therefore refer both to the protease as a substance and to the corresponding method, in particular method for manufacturing the protease.

Associated with the proteases in accordance with various embodiments and the manufacturing methods for proteases according to the various embodiments, as further embodiments are nucleic acids coding for said proteases, proteases or nucleic acids according to the embodiments containing non-human host cells, as well as agents, in particular washing and cleaning agents, washing and cleaning methods, and uses defined by way of proteases according to the embodiments, encompassing proteases according to the embodiments. In addition, other objects, desirable features and characteristics will become apparent from the subsequent summary and detailed description, and the appended claims, taken in conjunction with the accompanying drawings and this background.

It has been found, surprisingly, that a modification according to the embodiments of position 21 in a protease that encompasses an amino acid sequence at least 70% identical to the amino acid sequence indicated in SEQ ID NO. 1 brings about improved performance of that modified protease in washing and cleaning agents, as compared with a corresponding protease that does not exhibit these modifications. This is surprising in particular because the protease modified according to the embodiments is markedly different from further subtilisins established in the existing art, such as e.g. subtilisin 309, PB92, the alkaline protease from *Bacillus lentus* DSM 5483, or BPN', etc. For example, a protease having SEQ ID NO. 1 is 78.4% identical to subtilisin 309, 78.1% identical to PB92, 77.7% identical to the alkaline protease from *Bacillus lentus* DSM 5483, and 55.3% identical to BPN', where SEQ ID NO. 1 discloses the sequence of the mature protease from *Bacillus gibsonii* (DSM 14391). It was therefore in no way to be expected that, for proteases of the type of an alkaline protease from *Bacillus gibsonii* (DSM 14391), protease variants having improved performance for use in washing and cleaning agents would be obtained by a modification at position 21 in the count of the alkaline protease from *Bacillus gibsonii* (DSM 14391), with respect to the mature enzyme in accordance with SEQ ID NO. 1.

Embodiments of proteases contemplated herein make, for example, a contribution to the cleaning performance of a washing or cleaning agent that contains the protease which is sufficiently good that it approaches the contribution to the cleaning performance of the agent of a proteolytic enzyme established for that purpose, and on various stains in fact exceeds it. Proteases contemplated herein consequently make possible improved removal of at least one, preferably multiple protease-sensitive stains on textiles and/or hard surfaces, for example tableware. Particularly advantageous cleaning performance effects are exhibited by preferred embodiments of proteases on chocolate- or cocoa-containing stains. Embodiments contemplated herein thus furnish stain-specific proteases whose cleaning performance is specifically advantageous with regard to one stain or multiple stains of similar type. The spot focus of preferred embodiments of proteases herein with regard to chocolate- or cocoa-containing stains is consequently improved.

Embodiments of proteases contemplated herein already achieve such advantageous cleaning performance effects even at low temperatures between 10° C. and 40° C., between 10° C. and 30° C., and between 10° C. and 25° C., for example at 20° C.

In addition, Embodiments of proteases contemplated herein possess particular stability with respect to surfactants and/or bleaching agents and/or with respect to temperature influences, in particular with respect to high or low temperatures and/or with respect to acid or alkaline conditions and/or with respect to changes in pH and/or with respect to denaturing or oxidizing agents and/or with respect to proteolytic breakdown and/or with respect to a change in redox conditions.

A protease to an embodiment exhibits a proteolytic activity, i.e. it is capable of hydrolyzing peptide bonds of a polypeptide, for example, of a protein, in particular in a washing or cleaning agent. A protease contemplated herein is therefore an enzyme that catalyzes the hydrolysis of peptide bonds and is thereby capable of cleaving peptides or proteins.

A protease of an embodiment is suitable, on the basis of its proteolytic activity and/or its further properties, in particular in relation to its stability with respect to surfactants and/or bleaching agents and/or its temperature profile and/or its pH profile, for use in washing and cleaning agents. It therefore makes possible improved removal of at least one, preferably multiple protease-sensitive stains on textiles and/or hard surfaces, for example tableware. Particularly advantageous cleaning performance effects are exhibited by proteases contemplated herein, for example, on stains containing grass, egg, chocolate milk, carbon black, cocoa, blood, milk, and mixtures thereof, for example the following stains:

grass on cotton: product no. 164 obtainable from Eidgenössische Material-und Prüfanstalt (EMPA) Testmaterialen AG [Swiss federal materials and testing agency test materials], St. Gallen, Switzerland, whole egg/pigment (whole egg/carbon black) on cotton: product no. 10N of wfk Testgewebe GmbH [Test fabrics], Brüggen-Bracht, Germany, chocolate milk/carbon black on cotton: product no. C-03 obtainable from CFT (Center For Testmaterials) B.V., Vlaardingen, Netherlands, cocoa on cotton: product no. 112 obtainable from Eidgenössische Material-und Prüanstalt (EMPA) Testmaterialen AG, St. Gallen, Switzerland, blood-milk/ink on cotton: product no. C-05 obtainable from CFT (Center For Testmaterials) B.V., Vlaardingen, Netherlands.

The proteases contemplated herein are very particularly advantageously effective on chocolate- or cocoa-containing stains, for example the stains C-03 and/or EMPA 112 recited above.

Also surprisingly, it has been found that such advantageous cleaning performance effects are achieved even at low temperatures between 10° C. and 40° C., between 10° C. and 30° C., and between 10° C. and 25° C., for example at 20° C.

"Cleaning performance" is understood in the context herein as brightening performance on one or more stains, in particular on laundry or tableware. Herein, both the washing or cleaning agent that encompasses the protease resp. the washing resp. cleaning bath constituted by said agent, and the protease itself, has a respective cleaning performance. The cleaning performance of the enzyme thus contributes to the cleaning performance of the agent and of the washing and/or cleaning bath constituted by the agent. The cleaning performance is preferably ascertained as indicated below.

In a further embodiment, the protease encompasses an amino acid sequence that is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, and very particularly preferably 99.5% identical to the amino acid sequence indicated in SEQ ID NO. 1 over its entire length, and comprises the amino acid substitution I21V in the count in accordance with SEQ ID NO. 1. In a preferred embodiment, the protease encompasses an amino acid sequence that matches the amino acid sequence indicated in SEQ ID NO. 1 in positions 1 to 20 and 22 to 269, and exhibits the amino acid substitution I21V in the count in accordance with SEQ ID NO. 1. A preferred protease of this kind is indicated under SEQ ID NO. 2, i.e. a protease according to an embodiment preferably encompasses SEQ ID NO. 2.

Surprisingly, it has also been found that further alternative possibilities exist for modifying the amino acid present in position 21 in order to obtain an improvement in the performance of the resulting protease. What is fundamentally important is that the protease be in fact modified with respect to SEQ ID NO. 1 at that position, i.e. that the amino acid present at that position be replaced by another proteinogenic amino acid, i.e. by alanine or arginine or asparagine or aspartic acid or cysteine or glutamine or glutamic acid or glycine or histidine or leucine or lysine or methionine or phenylalanine or proline or serine or threonine or tryptophan or tyrosine or, in particular, valine. Because valine is particularly advantageous at this position, of the foregoing amino acids, amino acids conservative with respect to valine are preferred, i.e. those that (to the extent valine is replaced by such an amino acid) do not result in a change in polarity or charge, in particular glycine, alanine, isoleucine, leucine, and methionine.

The identity of nucleic acid sequences or amino acid sequences is determined by means of a sequence comparison. This sequence comparison is based on the BLAST algorithm that is established in the existing art and usually used (cf. for example Altschul, S. F., Gish, W., Miller, W., Myers, E. W., & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs", Nucleic Acids Res., 25, pp. 3389-3402), and is effected in principle by mutually associating similar successions of nucleotides or amino acids in the nucleic acid sequences resp. amino acid sequences. A tabular association of the relevant positions is referred to as an "alignment." A further algorithm available in the existing art is the FASTA algorithm. Sequence comparisons (alignments), in particular multiple sequence comparisons, are prepared using computer programs. The Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217), or programs based on these programs or algorithms, are often used. Herein, all the sequence comparisons (alignments) were prepared using the computer program Vector NTI® Suite 10.3 (Invitrogen Corporation, 1600 Faraday Avenue, Carlsbad, Calif., USA) with the predefined default parameters, whose AlignX module for the sequence comparisons is based on ClustalW.

A comparison of this kind also allows a statement as to the similarity to one another of the sequences that are being compared. This is usually indicated as a percentage identity, i.e. the proportion of identical nucleotides or amino acid residues at the same positions resp. in positions corresponding to one another in an alignment. The more broadly construed term "homology" also, in the context of amino acid sequences, incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous resp. identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity resp. homology herein refer to the full length of the respectively indicated nucleic acid sequence or amino acid sequence.

In a further embodiment, the protease is characterized in that its cleaning performance corresponds at least to that of a protease that encompasses an amino acid sequence that corresponds to the amino acid sequence indicated in SEQ ID NO. 1, and/or at least to that of a protease that encompasses an amino acid sequence that corresponds to the amino acid sequence indicated in SEQ ID NO. 2, and/or at least to that of a protease in accordance with SEQ ID NO. 3, the cleaning performance being determined in a washing system that contains a washing agent at a dosing ratio of between 4.5 and 7.0 grams per liter of washing bath as well as the protease, the proteases to be compared being used on an equal-activity basis and the cleaning performance being determined with respect to one or more of the following stains: blood-milk/ink on cotton, chocolate-milk/carbon black on cotton, peanut oil-pigment/ink on polyester/cotton, and grass on cotton, in particular with respect to one or more of the following stains:

blood-milk/ink on cotton: product no. C-05 obtainable from CFT (Center for Testmaterials) B.V., Vlaardingen, Netherlands, chocolate-milk/carbon black on cotton: product no. C-03 obtainable from CFT (Center for Testmaterials) B.V., Vlaardingen, Netherlands, peanut oil-pigment/ink on polyester/cotton: product no. PC-10 obtainable from CFT (Center for Testmaterials) B.V., Vlaardingen, Netherlands, grass on cotton: product no. 164 obtainable from Eidgenössische Material-und Prüanstalt (EMPA) Testmaterialien AG, St. Gallen, Switzerland, by measuring the whiteness of the washed textiles, the washing procedure being performed for at least 30 minutes, optionally 60 minutes, at a temperature of 40° C., and the water having a water hardness between 15.5 and 16.5° (German degrees of hardness).

A preferred liquid washing agent for a washing system of this kind has the following composition (all indications in percentage by weight): 0.3 to 0.5% xanthan, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1% boric acid, 1 to 2% sodium citrate (dihydrate), 2 to 4% soda, 14 to 16% coconut fatty acid, 0.5% HEDP (1-hydroxyethane-(1,1-diphosphonic acid)), 0 to 0.4% PVP (polyvinylpyrrolidone), 0 to 0.05% optical brightener, 0 to 0.001% dye, remainder deionized water. The dosing ratio of the liquid washing agent is preferably between 4.5 and 6.0 grams per liter of washing bath, for example 4.7, 4.9, or 5.9 grams per liter of washing bath. Washing preferably occurs in a pH range between pH 8 and pH 10.5, preferably between pH 8 and pH 9.

A preferred powdered washing agent for a washing system of this kind has the following composition (all indications in percentage by weight): 10% linear alkylbenzenesulfonate (sodium salt), 1.5% C12 to C18 fatty alcohol sulfate (sodium salt), 2.0% C12 to C18 fatty alcohol with 7 EO, 20% sodium carbonate, 6.5% sodium hydrogencarbonate, 4.0% amorphous sodium disilicate, 17% sodium carbonate peroxohydrate, 4.0% TAED, 3.0% polyacrylate, 1.0% carboxymethyl cellulose, 1.0% phosphonate, 25% sodium sulfate; remainder: foam inhibitors, optical brighteners, scents. The dosing ratio of the powdered washing agent is preferably between 5.5 and 7.0 grams per liter of washing bath, for example 5.6, 5.9, or 6.7 grams per liter of washing bath. Washing preferably occurs in a pH range between pH 9 and pH 11.

Determination of the cleaning performance at 40° C. is performed using a solid washing agent as indicated above.

The whiteness, i.e. the brightening of the stains, is determined as an indication of washing performance, preferably using optical measurement methods, preferably photometrically. A device suitable for this is, for example, the Minolta CM508d spectrometer. The devices used for measurement are usually calibrated beforehand using a white standard, preferably a white standard provided with the unit.

Equal-activity utilization of the respective protease ensures that the respective enzymatic properties, i.e. for example the cleaning performance on specific stains, are compared even if there is some drifting apart of the ratio of active substance to total protein (the values for specific activity). It is generally the case that a low specific activity can be compensated for by adding a larger quantity of protein. Methods for determining protease activities are familiar to one skilled in the art of enzyme technology, and are applied by him or her on a routine basis. Such methods are disclosed, for example, in Tenside, Vol. 7 (1970), pp. 125-132. Alternatively, the protease activity can be determined quantitatively by way of the release of para-nitroaniline (pNA) chromophore from the suc-L-Ala-L-Ala-L-Pro-L-Phe-p-nitroanilide substrate (AAPF). The protease cleaves the substrate and releases pNA. The release of pNA causes an increase in extinction at 410 nm, the change in which over time is an indication of enzymatic activity (see Del Mar et al., 1979). Measurement is performed at a temperature of 25° C., at pH 8.6, and a wavelength of 410 nm. The measurement time is 5 min, and the measurement interval 20 s to 60 s.

The protein concentration can be determined with the aid of known methods, for example the BCA method (bichinchoninic acid; 2,2'-biquinolyl-4,4'-dicarboxylic acid) or the biuret method (A. G. Gornall, C. S. Bardawill and M. M. David, J. Biol. Chem., 177 (1948), pp. 751-766). The active protein concentration can be determined, in this regard, by titrating the active centers using a suitable irreversible inhibitor (for proteases, for example, phenylmethylsulfonyl fluoride (PMSF)), and determining the residual activity (cf. M. Bender et al., J. Am. Chem. Soc. 88, 24 (1966), pp. 5890-5913).

The protease activity is usually indicated in protease units (PU). Suitable protease activities, for example, are 2.5, 5 or 10 PU per ml of washing bath. The protease activity is not, however, equal to zero.

In addition to the amino acid modifications explained above, proteases according to the embodiments can comprise further amino acid modifications, in particular amino acid substitutions, insertions, or deletions. Such proteases are, for example, further developed by targeted genetic modification, i.e. by way of mutagenesis methods, and optimized for specific purposes or with regard to special properties (for example, with regard to their catalytic activity, stability, etc.). In addition, nucleic acids contemplated herein can be introduced into recombination formulations and thereby used to generate entirely novel proteases or other polypeptides.

The objective is to introduce targeted mutations, such as substitutions, insertions, or deletions, into the known molecules in order, for example, to improve the cleaning performance of enzymes as contemplated herein. For this purpose, in particular, the surface charges and/or isoelectric point of the molecules, and thereby their interactions with the substrate, can be modified. For example, the net charge of the enzymes can be modified in order thereby to influence substrate bonding, in particular for use in washing and cleaning agents. Alternatively or additionally, the stability of the protease can be enhanced by way of one or more corresponding mutations, and its cleaning performance thereby improved. Advantageous properties of individual mutations, e.g. individual substitutions, can supplement one another. A protease already optimized with regard to specific properties, for example with regard to its stability in terms of surfactants and/or bleaching agents and/or other components, can therefore be additionally further developed in the context of the invention.

The following convention is used to describe substitutions that relate to exactly one amino acid position (amino acid exchanges): Firstly the amino acid that is naturally present is designated in the form of the internationally usual single-letter code; this is followed by the relevant sequence position, and lastly by the inserted amino acid. Multiple exchanges within the same polypeptide chain are separated from one another by slashes. For insertions, additional amino acids are named after the sequence position. For deletions, the missing amino acid is replaced by a symbol, for example an asterisk or a dash. For example, "A95G" describes the substitution of alanine at position 95 with glycine; "A95AG" describes the insertion of glycine after the amino acid alanine at position 95; and "A95*" describes the deletion of alanine at position 95. This nomenclature is known to one skilled in the art of enzyme technology.

In another embodiment therefore, a protease is characterized in that it is obtainable from a protease as described above as an initial molecule by single or multiple conservative amino acid substitution, the protease exhibiting the amino acid substitution I21V in the count in accordance with SEQ ID NO. 1. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I=V=L=M, D=E, N=Q, K=R, Y=F, S=T, G=A=I=V=L=M=Y=F=W=P=S=T.

Alternatively or additionally, the protease is characterized in that it is obtainable from a protease contemplated herein as an initial molecule by fragmentation or by deletion, insertion, or substitution mutagenesis, and encompasses an amino acid sequence that matches the initial molecule over a length of at least 50, 60, 70, 80, 90, 100, 110, 120, 130, 140, 150, 160, 170, 180, 190, 200, 210, 220, 230, 240, 250, 260, 265, 266, or 267 continuously connected amino acids, the amino acid substitution I12V contained in the initial molecule still being present.

It is thus possible, for example, to delete individual amino acids at the termini or in the loops of the enzyme with no loss of or diminution in proteolytic activity as a result. Furthermore, for example, the allergenicity of relevant enzymes can also be decreased by way of such fragmentation or deletion, insertion, or substitution mutagenesis, thus improving its overall usability. Advantageously, the enzymes retain their proteolytic activity even after mutagenesis, i.e. their proteolytic activity corresponds at least to that of the initial enzyme. Substitutions, too, can exhibit advantageous effects. Both individual and multiple continuously connected amino acids can be exchanged for other amino acids.

Alternatively or additionally, the protease is characterized in that it is obtainable from a protease contemplated herein as an initial molecule by way of one or more amino acid substitutions in positions that are associated in an alignment with the positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255, and 268 of the protease from *Bacillus lentus* in accordance with SEQ ID NO. 3, such that the protease exhibits the amino acid substitution I21V in the count in accordance with SEQ ID NO. 1. The further amino acid positions are defined here by an alignment of the amino acid sequence of a protease according to the various embodiments herein with the amino acid sequence of the protease from *Bacillus lentus* as indicated in SEQ ID NO. 3. An alignment of this kind is indicated in FIG. 1. Because the protease from *Bacillus lentus* represents an important reference molecule in the existing art for describing new proteases and amino acid modifications, and the new proteases described here (and thus also their sequence) are hitherto unknown, it is advantageous to make reference to the protease from *Bacillus lentus* (SEQ ID NO. 3) in the association of the amino acid positions. The association of the positions is furthermore directed toward the mature protein. This association is also to be utilized, in particular, when the amino acid sequence of a protease contemplated herein encompasses a greater number of amino acid residues than the protease from *Bacillus lentus* in accordance with SEQ ID NO. 3. Proceeding from the aforesaid positions in the amino acid sequence of the protease from *Bacillus lentus*, the modification positions in a protease herein are those that are in fact associated with those positions in an alignment, for example in accordance with FIG. 1.

Advantageous positions for sequence modifications, in particular substitutions, of the protease from *Bacillus lentus* that, transferred to homologous positions of the proteases contemplated herein, are preferably of significance and impart advantageous functional properties to the protease, are accordingly to be associated with the positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255, and 268 in an alignment with SEQ ID NO. 3 and thus in the count in accordance with SEQ ID NO. 3. The amino acid residues located in the aforesaid positions in the wild type molecule of the protease from *Bacillus lentus* are the following: S3, V4, S36, N42, A47, T56, G61, T69, E87, A96, R99, A101, I102, S104, N114, H118, A120, S130, S139, T141, S142, S154, S157, A188, V193, V199, G205, L211, A224, K229, S236, N237, N242, H243, N255, respectively T268.

Substitutions 3T, 4I, 61A, 99G, 99A, 99S, 99E, 154D, 154E, 211D, 211G, and 211E, for example, are particularly advantageous, to the extent the correspondingly homologous positions in a protease contemplated herein are not already naturally occupied by one of these preferred amino acids. The exchanges 3T and 4I result, by way of a stabilizing effect on the molecule, in an improvement in the cleaning performance of the protease and thus in improved cleaning performance of a washing or cleaning agent that contains the protease.

A further confirmation of a correct association of the amino acids to be modified, i.e. in particular their functional correspondence, can be supplied by comparison experiments in which the two positions associated with one another on the basis of an alignment are modified in the same way in both of the proteases being compared with each other, and an observation is made as to whether the enzymatic activity of the two is modified in the same way. For example, if an amino acid exchange at a specific position of the protease from *Bacillus lentus* in accordance with SEQ ID NO. 3 is accompanied by a modification of an enzymatic parameter, for example an elevation of the KM value, and if a corresponding modification of the enzymatic parameter, for example therefore likewise an elevation of the KM value, is observed in a protease variant contemplated herein whose amino acid exchange was achieved by way of the same introduced amino acid, this is to be viewed as such a confirmation.

All the aforementioned facts are also applicable to the method for manufacturing a protease contemplated herein. A method according to an exemplary embodiment therefore further encompasses one or more of the following method steps:

introducing a single or multiple conservative amino acid substitution, such that the protease exhibits the amino acid substitution I21V in the count in accordance with SEQ ID NO. 1;

modifying the amino acid sequence by fragmentation or by deletion, insertion, or substitution mutagenesis, in such a way that the protease encompasses an amino acid sequence that matches the initial molecule over a length of at least 50, 60, 70, 80, 90, 100, 110, 120, 130, 140, 150, 160, 170, 180, 190, 200, 210, 220, 230, 240, 250, 260, 265, 266, or 267 continuously connected amino acids, the amino acid substitution I12V contained in the initial molecule still being present; and introducing a single or multiple amino acid substitution into one or more of the positions that are associated in an alignment with the positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255, and 268 of the protease from *Bacillus lentus* in accordance with SEQ ID NO. 3, such that the protease exhibits the amino acid substitution I21V in the count in accordance with SEQ ID NO. 1.

All the statements also apply to the methods contemplated herein.

In further embodiments, the protease resp. the protease manufactured with a method contemplated herein is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical to the amino acid sequence indicated in SEQ ID NO. 1 over its entire length. The protease resp. the protease manufactured with a method contemplated herein exhibits the amino acid substitution I21V.

According to another embodiment, a protease as described above is characterized in that it exhibits at least one chemical modification. A protease having such a modification is referred to as a derivative, i.e. the protease is derivatized.

For purposes contemplated herein, "derivatives" are accordingly understood as those proteins whose pure amino acid chain has been chemically modified. Such derivatization operations can be performed, for example, in vivo by the host cell that expresses the protein. Linkages of low-molecular-weight compounds, such as of lipids or oligosaccharides, are particularly to be emphasized in this context. Derivatizations can also, however, be carried out in vitro, e.g. by chemical conversion of a side chain of an amino acid, or by covalent bonding of a different compound onto the protein. Linkage of amines to carboxyl groups of an enzyme in order to modify the isoelectric point is, for example, possible. Another such compound can also be a further protein that is bound, for example, via bifunctional chemical compounds to a protein contemplated herein. "Derivatization" is likewise to be understood as covalent bonding to a macromolecular carrier, or also as a non-covalent inclusion into suitable macromolecular cage structures. Derivatizations can, for example, influence the substrate specificity or strength of bonding to the substrate, or can bring about a temporary blockage of enzymatic activity if the linked-on substance is an inhibitor. This can be useful, for example, for the period of storage.

Modifications of this kind can furthermore influence stability or enzymatic activity. They can moreover also serve to decrease the allergenicity and/or immunogenicity of the protein and thereby, for example, increase its skin compatibility. For example, linkages to macromolecular compounds, for example polyethylene glycol, can improve the protein with regard to stability and/or skin compatibility.

"Derivatives" of a protein contemplated herein can also be understood in the broadest sense as preparations of said proteins. Depending on recovery, processing, or preparation, a protein can be brought into association with a variety of other substances, for example from the culture of the producing microorganisms. A protein can also have had other substances deliberately added to it, for example in order to enhance its shelf stability. All preparations of a protein contemplated herein are therefore also contemplated herein. This is also irrespective of whether or not it actually displays this enzymatic activity in a specific preparation. This is because it may be desirable for it to possess little or no activity during storage, and to perform its enzymatic function only at the time of use. This can be controlled, for example, by way of corresponding accompanying substances. The preparation of proteases together with protease inhibitors is particularly advantageous.

With respect to all the proteases resp. protease variants and/or derivatives described above, those whose activity corresponds at least to that of the protease in accordance with SEQ ID NO. 1 and/or SEQ ID NO. 2 and/or SEQ ID NO. 3, and/or whose cleaning performance corresponds at least to that of the protease in accordance with SEQ ID NO. 1 and/or SEQ ID NO. 2 and/or SEQ ID NO. 3, are particularly preferred, the cleaning performance being determined in a washing system as described above.

In another embodiment, a nucleic acid codes for a protease as contemplated herein, as well as a vector containing such a nucleic acid, in particular a copying vector or an expression vector.

These can be DNA molecules or RNA molecules. They can exist as an individual strand, as an individual strand complementary to said individual strand, or as a double strand. With DNA molecules in particular, the sequences of both complementary strands in all three possible reading frames are to be considered in each case. Also to be considered is the fact that different codons, i.e. base triplets, can code for the same amino acids, so that a specific amino acid sequence can be coded by multiple different nucleic acids. As a result of this degeneracy of the genetic code, all nucleic acid sequences that can encode one of the above-described proteases are included in this subject of the invention. The skilled artisan is capable of unequivocally determining these nucleic acid sequences, since despite the degeneracy of the genetic code, defined amino acids are to be associated with individual codons. The skilled artisan can therefore, proceeding from an amino acid sequence, readily ascertain nucleic acids coding for that amino acid sequence. In addition, in the context of nucleic acids according to the present invention one or more codons can be replaced by synonymous codons. This aspect refers in particular to heterologous expression of the enzymes contemplated herein. For example, every organism, e.g. a host cell of a production strain, possesses a specific codon usage. "Codon usage" is understood as the translation of the genetic code into amino acids by the respective organism. Bottlenecks in protein biosynthesis can occur if the codons located on the nucleic acid are confronted, in the organism, with a comparatively small number of loaded tRNA molecules. Also it codes for the same amino acid, the result is that a codon becomes translated in the organism less efficiently than a synonymous codon that codes for the same amino acid. Because of the presence of a larger number of tRNA molecules for the synonymous codon, the latter can be translated more efficiently in the organism.

An example of a particularly preferred nucleic acid is indicated in SEQ ID NO. 4.

By way of methods commonly known today such as, for example, chemical synthesis or the polymerase chain reaction (PCR) in combination with standard methods of molecular biology or protein chemistry, a skilled artisan has the ability to manufacture, on the basis of known DNA sequences and/or amino acid sequences, the corresponding nucleic acids all the way to complete genes. Such methods are known, for example, from Sambrook, J., Fritsch, E. F., and Maniatis, T, 2001, Molecular cloning: a laboratory manual, 3rd edition, Cold Spring Laboratory Press.

"Vectors" are understood for purposes herein as elements, made up of nucleic acids, that contain a nucleic acid contemplated herein as a characterizing nucleic acid region. They enable said nucleic acid to be established as a stable genetic element in a species or a cell line over multiple generations or cell divisions. In particular when used in bacteria, vectors are special plasmids, i.e. circular genetic elements. In the context herein, a nucleic acid as contemplated herein is cloned into a vector. Included among the vectors are, for example, those whose origins are bacterial plasmids, viruses, or bacteriophages, or predominantly synthetic vectors or plasmids having elements of widely differing derivations. Using the further genetic elements present in each case, vectors are capable of establishing themselves as stable units in the relevant host cells over multiple generations. They can be present extrachromosomally as separate units, or can be integrated into a chromosome resp. into chromosomal DNA.

Expression vectors encompass nucleic acid sequences which are capable of replicating in the host cells, by preference microorganisms, particularly preferably bacteria, that contain them, and expressing therein a contained nucleic acid. Expression is influenced in particular by the promoter or promoters that regulate transcription. Expression can occur in principle by means of the natural promoter originally located in front of the nucleic acid to be expressed, but also by means of a host-cell promoter furnished on the expression vector or also by means of a modified, or entirely different, promoter of another organism or of another host cell. In the present case at least one promoter for expression of a nucleic acid as contemplated herein is made available and used for expression thereof. Expression vectors can furthermore be regulatable, for example by way of a change in culture conditions or when the host cells containing them reach a specific cell density, or by the addition of specific substances, in particular activators of gene expression. One example of such a substance is the galactose derivative isopropyl-β-D-thiogalactopyranoside (IPTG), which is used as an activator of the bacterial lactose operon (lac operon). In contrast to expression vectors, the contained nucleic acid is not expressed in cloning vectors.

In a further embodiment, a non-human host cell contains a nucleic acid as contemplated herein or a vector as contemplated herein, or that contains a protease as contemplated herein, in particular one that secretes the protease into the medium surrounding the host cell. A nucleic acid as contemplated herein resp. a vector as contemplated herein is preferably transformed into a microorganism, which then represents a host cell according to an embodiment. Alternatively, individual components, i.e. nucleic acid parts resp. fragments of a nucleic acid contemplated herein, can be also be introduced into a host cell in such a way that the host cell which then results contains a nucleic acid contemplated herein resp.

a vector contemplated herein. This procedure is suitable in particular when the host cell already contains one or more constituents of a nucleic acid contemplated herein resp. a vector contemplated herein, and the further constituents are then correspondingly supplemented. Methods for the transformation of cells are established in the existing art and are sufficiently known to the skilled artisan. All cells are in principle suitable as host cells, i.e. prokaryotic or eukaryotic cells. Those host cells that can be manipulated in genetically advantageous fashion, e.g. as regards transformation using the nucleic acid or vector and stable establishment thereof, are preferred, for example single-celled fungi or bacteria. In addition, preferred host cells are notable for being readily manipulated in microbiological and biotechnological terms. This refers, for example, to easy culturability, high growth rates, low demands in terms of fermentation media, and good production and secretion rates for foreign proteins. Preferred host cells contemplated herein secrete the (transgenically) expressed protein into the medium surrounding the host cells. The proteases can furthermore be modified, after their manufacture, by the cells producing them, for example by the addition of sugar molecules, formylation, amination, etc. Post-translation modifications of this kind can functionally influence the protease.

Further embodiments are represented by those host cells whose activity can be regulated on the basis of genetic regulation elements that are made available, for example, on the vector, but can also be present a priori in those cells. They can be stimulated to expression, for example, by controlled addition of chemical compounds that serve as activators, by modifying the culture conditions, or when a specific cell density is reached. This makes possible economical production of the proteins contemplated herein. One example of such a compound is IPTG, as described earlier.

Preferred host cells are prokaryotic or bacterial cells. Bacteria are notable for short generation times and few demands in terms of culturing conditions. As a result, economical culturing methods resp. manufacturing methods can be established. In addition, the skilled artisan has ample experience in the context of bacteria in fermentation technology. Gram-negative or Gram-positive bacteria may be suitable for a specific production instance, for a wide variety of reasons to be ascertained experimentally in the individual case, such as nutrient sources, product formation rate, time requirement, etc.

In Gram-negative bacteria such as, for example, *Escherichia coli*, a plurality of proteins are secreted into the periplasmic space, i.e. into the compartment between the two membranes enclosing the cell. This can be advantageous for specific applications. Gram-negative bacteria can furthermore also be configured so that they discharge the expressed proteins not only into the periplasmic space but into the medium surrounding the bacterium. Gram-positive bacteria, on the other hand, such as e.g. bacilli or actinomycetes, or other representatives of the actinomycetals, possess no external membrane, so that secreted proteins are delivered immediately into the medium, as a rule the nutrient medium, surrounding the bacteria, from which medium the expressed proteins can be purified. They can be isolated directly from the medium, or further processed. In addition, Gram-positive bacteria are related or identical to most originating organisms for technically important enzymes, and usually themselves form comparable enzymes, so that they possess similar codon usage and their protein synthesis apparatus is of course correspondingly directed.

Host cells contemplated herein can be modified in terms of their requirements for culture conditions, can comprise other or additional selection markers, or can also express other or additional proteins. They can, in particular, be those host cells that transgenically express multiple proteins or enzymes.

The various embodiments herein are applicable in principle to all microorganisms, in particular to all fermentable microorganisms, particularly preferably to those of the genus *Bacillus*, and the result is that proteins contemplated herein can be manufactured by the use of such microorganisms. Such microorganisms then represent host cells for purposes herein.

In a further embodiment, the host cell is characterized in that it is a bacterium, preferably one that is selected from the group of the genera *Escherichia, Klebsiella, Bacillus, Staphylococcus, Corynebacterium, Arthrobacter, Streptomyces, Stenotrophomonas*, and *Pseudomonas*, more preferably one that is selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor*, and *Stenotrophomonas maltophilia*.

The host cell can, however, also be a eukaryotic cell, which is characterized in that it possesses a cell nucleus. A further embodiment is therefore represented by a host cell which is characterized in that it possesses a cell nucleus. In contrast to prokaryotic cells, eukaryotic cells are capable of post-translationally modifying the protein that is formed. Examples thereof are fungi such as Actinomycetes, or yeasts such as *Saccharomyces* or *Kluyveromyces*. This may be particularly advantageous, for example, when the proteins, in connection with their synthesis, are intended to experience specific modifications made possible by such systems. Among the modifications that eukaryotic systems carry out in particular in conjunction with protein synthesis are, for example, the bonding of low-molecular-weight compounds such as membrane anchors or oligosaccharides. Oligosaccharide modifications of this kind can be desirable, for example, in order to lower the allergenicity of an expressed protein. Co-expression with the enzymes naturally formed by such cells, for example cellulases or lipases, can also be advantageous. Thermophilic fungal expression systems, for example, can furthermore be particularly suitable for the expression of temperature-resistant proteins or variants.

The host cells contemplated herein are cultured and fermented in a usual manner, for example in discontinuous or continuous systems. In the former case a suitable nutrient medium is inoculated with the host cells, and the product is harvested from the medium after a period of time to be ascertained experimentally. Continuous fermentations are notable for the achievement of a flow equilibrium in which, over a comparatively long period of time, cells die off in part but are also in part renewed, and the protein formed can simultaneously be removed from the medium.

Host cells contemplated herein are preferably used to manufacture proteases contemplated herein. A further embodiment is therefore a method for manufacturing a protease, encompassing culturing a host cell contemplated herein; and isolating the protease from the culture medium or from the host cell.

Another embodiment preferably encompasses fermentation methods. Fermentation methods are known from the existing art and represent the actual industrial-scale production step, generally followed by a suitable method for purifying the product that was manufactured, for example the protease contemplated herein. All fermentation methods that are based on a corresponding method for manufacturing a protease contemplated herein correspondingly represent embodiments herein.

Fermentation methods which are characterized in that fermentation is carried out by way of an inflow strategy are particularly appropriate. In this context the constituents of the medium that are consumed during continuous culturing are fed in. Considerable increases both in cell density and in cell mass resp. dry mass, and/or principally in the activity of the protease of interest, can thereby be achieved. In addition, the fermentation operation can also be configured so that undesired metabolic products are filtered out, or are neutralized by the addition of a buffer or respectively suitable counterions.

The protease that is manufactured can be harvested from the fermentation medium. A fermentation method of this kind is preferred over isolation of the protease from the host cells, i.e. product preparation from the cell mass (dry mass), but requires that suitable host cells, or one or more suitable secretion markers resp. mechanisms and/or transport systems, be made available so that the host cells secrete the protease into the fermentation medium. Alternatively, without secretion, isolation of the protease from the host cell can occur, i.e. purification thereof from the cell mass, for example by precipitation using ammonium sulfate or ethanol, or by chromatographic purification.

All the above facts can be combined into methods for manufacturing proteases as contemplated herein.

In another embodiment, an agent is characterized in that it contains a protease as contemplated herein and as described above. The agent is preferably a washing or cleaning agent. Because proteases as contemplated herein exhibit advantageous cleaning performance effects in particular on chocolate- or cocoa-containing stains, the agents are suitable and advantageous in particular for removing such stains.

All conceivable types of washing resp. cleaning agents, both concentrates and agents to be used undiluted, for use on a commercial scale, in washing machines, or for hand laundering resp. cleaning are contemplated herein. Included thereamong are, for example, washing agents for textiles, carpets, or natural fibers, for which the term "washing agent" is used. Also included thereamong are, for example, dishwashing agents for automatic dishwashers, or manual dishwashing agents, or cleaners for hard surfaces such as metal, glass, porcelain, ceramic, tiles, stone, painted surfaces, plastics, wood, or leather, for which the term "cleaning agent" is used, i.e. in addition to manual and automatic dishwashing agents, for example also scouring agents, glass cleaners, toilet cleaners, etc. Further included among the washing and cleaning agents herein are washing adjuvants that are dispensed into the actual washing agent in the context of manual or automatic textile laundering in order achieve a further effect. Also included among washing and cleaning agents herein are textile pre- and post-treatment agents, i.e. those agents with which the laundered item is brought into contact before actual laundering, for example in order to loosen stubborn stains, as well as those agents that, in a step following actual textile laundering, impart to the washed item further desirable properties such as a pleasant feel, absence of creases, or low static charge. The fabric softeners, among others, are classified among the latter agents.

The washing or cleaning agents as contemplated herein, which can be present as in particular powdered solids, in recompressed particle form, as homogeneous solutions or suspensions, can contain alongside a protease as contemplated herein all known ingredients usual in such agents, at least one further ingredient preferably being present in the agent. The agents as contemplated herein can contain, in particular, surfactants, builders, peroxygen compounds, or bleach activators. They can further contain water-miscible organic solvents, further enzymes, sequestering agents, electrolytes, pH regulators, and/or further adjuvants such as optical brighteners, anti-gray agents, foam regulators, as well as dyes and scents, as well as combinations thereof.

A combination of a protease as contemplated herein with one or more further ingredient(s) of the agent is particularly advantageous, since such an agent exhibits improved cleaning performance thanks to synergies that result. Such a synergy can be achieved in particular by combining a protease as contemplated herein with a surfactant and/or a builder (detergency builder) and/or a peroxygen compound and/or a bleach activator.

Advantageous ingredients of agents as contemplated herein are disclosed in the international patent application WO 2009/121725, beginning therein on page 5, next-to-last paragraph and ending on page 13 after the second paragraph. Reference is expressly made to this disclosure, and the disclosure therein is incorporated in its entirety herein.

An agent as contemplated herein contains the protease advantageously in a quantity of from about 2 μg to about 20 mg, by preference from about 5 μg to about 17.5 mg, particularly preferably from about 20 μg to about 15 mg, and very particularly preferably from about 50 μg to about 10 mg per g of the agent. In addition, the protease contained in the agent, and/or further ingredients of the agent, can be encased with a substance that is impermeable to the enzyme at room temperature or in the absence of water, which substance becomes permeable to the enzyme under utilization conditions of the agent. Such an embodiment is thus characterized in that the protease is encased with a substance that is impermeable to the protease at room temperature or in the absence of water. In addition, the washing or cleaning agent itself can also be packaged in a container, by preference an air-permeable container, from which it is released shortly before use or during the washing operation.

In further embodiments, the agent is characterized in that it is:

present in solid form, in particular as a pourable powder having a bulk weight from about 300 g/l to about 1200 g/l, in particular about 500 g/l to about 900 g/l, or present in pasty or in liquid form, and/or present as a one-component system, or distributed into multiple components.

These embodiments encompass all solid, powdered, liquid, gelled, or pasty administration forms of agents as contemplated herein, which optionally can also be made up of multiple phases and can be present in compressed or uncompressed form. The agent can be present as a pourable powder, in particular having a bulk weight from about 300 g/l to about 1200 g/l, in particular about 500 g/l to about 900 g/l, or about 600 g/l to about 850 g/l. Further included among the solid administration forms of the agent are extrudates, granulates, tablets, or pouches. Alternatively, the agent can also be liquid, gelled, or pasty, for example in the form of a nonaqueous liquid washing agent or a nonaqueous paste or in the form of an aqueous liquid washing agent or a hydrous paste. The agent can furthermore be present as a one-component system. Such agents are made up of one phase. Alternatively, an agent can also be made up of multiple phases. An agent of this kind is thus distributed into multiple components.

Washing or cleaning agents as contemplated herein can contain exclusively a protease as contemplated herein. Alternatively, they can also contain further hydrolytic enzymes or other enzymes, in a concentration useful for the effectiveness of the agent. A further embodiment is thus represented by agents that moreover encompass one or more further enzymes. All enzymes that can display catalytic activity in the agent as contemplated herein are preferably usable as further enzymes, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase, or a lipase, as well as mixtures thereof. Further enzymes are contained in the agent advantageously in a quantity in each case from 1×10-8 to 5 weight percent, based on active protein. Increasingly preferably, each further enzyme is contained in agents as contemplated herein in a quantity from about 1×10-7 to about 3 wt %, from about 0.00001 to about 1 wt %, from about 0.00005 to about 0.5 wt %, from about 0.0001 to about 0.1 wt %, and particularly preferably from 0.0001 to 0.05 wt %, based on active protein. Particularly preferably, the enzymes exhibit synergistic cleaning performance effects with respect to specific stains or spots, i.e. the enzymes contained in the agent composition mutually assist one another in their cleaning performance. Very particularly preferably, a synergism of this kind exists between the protease contained as contemplated herein and a further enzyme of an agent as contemplated herein, thereamong in particular between the aforesaid protease and the amylase and/or a lipase and/or a mannanase and/or a cellulase and/or a pectinase. Synergistic effects can occur not only between different enzymes, but also between one or more enzymes and further ingredients of the agent as contemplated herein.

A further embodiment is a method for cleaning textiles or hard surfaces which is characterized in that at least one method step an agent as contemplated herein is utilized; or that in at least one method step a protease as contemplated herein or a protease obtained according to a method as contemplated herein is catalytically active, in particular in such a way that the protease is used in a quantity from about 40 µg to about 4 g, by preference from about 50 µg to about 3 g, particularly preferably from about 100 µg to about 2 g, and very particularly preferably from about 200 µg to about 1 g, per utilization.

Included thereamong are both manual and automatic methods, automatic methods being preferred. Methods for cleaning textiles are generally notable for the fact that, in multiple method steps, various substances having cleaning activity are applied onto the material to be cleaned and are washed out after the contact time, or that the material to be cleaned is treated in another fashion with a washing agent or a solution resp. dilution of said agent. The same applies correspondingly to methods for cleaning all materials other than textiles, in particular hard surfaces. All conceivable washing or cleaning methods can be supplemented, in at least one of the method steps, by the utilization of a washing or cleaning agent as contemplated herein, and then represent embodiments herein. All facts, subject matters, and embodiments that are described for the proteases as contemplated herein resp. agents containing them are also applicable to washing and cleaning methods herein. Reference is therefore expressly made at this juncture to the disclosure at the corresponding juncture, with the instruction that this disclosure is also valid for the present methods.

Because proteases as contemplated herein already naturally possess a hydrolytic activity and display it even in media that otherwise possess no cleaning power, for example in pure buffer, an individual and/or the only step of such a method can consist in bringing such a protease, if desired as a sole component having cleaning activity, into contact with the stain, preferably in a buffer solution or in water. This represents a further embodiment herein.

Alternative embodiments are also represented by methods for treating textile raw materials or for textile care, in which a protease as contemplated herein becomes active in at least one method step. Preferred thereamong are methods for textile raw materials, fibers, or textiles having natural constituents, and very particularly for those having wool or silk.

A further embodiment is the use of an agent as contemplated herein for the cleaning of textiles or hard surfaces, or of a protease as contemplated herein or of a protease obtained according to a method as contemplated herein, for the cleaning of textiles or hard surfaces, in particular in such a way that the protease is used in a quantity from about 40 µg to about 4 g, by preference from about 50 µg to about 3 g, particularly preferably from about 100 µg to about 2 g, and very particularly preferably from about 200 µg to about 1 g, per utilization.

All facts, subject matters, and embodiments that are described for the proteases as contemplated herein resp. agents containing them are also applicable to this subject. Reference is therefore expressly made at this juncture to the disclosure at the corresponding juncture, with the instruction that this disclosure is also valid for the present method.

EXAMPLES

All the molecular-biological working steps follow standard methods such as those indicated, for example, in the manual of Fritsch, Sambrook, and Maniatis, "Molecular cloning: a laboratory manual," Cold Spring Harbor Laboratory Press, New York, 1989, or comparable relevant works. Enzymes and kits were used in accordance with the respective manufacturer's instructions.

Example 1

Proceeding from a protease that exhibited an amino acid sequence in accordance with SEQ ID NO. 1, a protease variant as contemplated herein was manufactured by site-directed mutagenesis in the nucleic acid coding for the protease, by means of the SeSaM method (Wong, T. S. et al. (2004): Sequence saturation mutagenesis (SeSaM): a novel method for directed evolution. Nucleic Acids Res. 32, 26 ff.). In this, the codon for the amino acid position 21 was modified from ATA to GTA, so that based on the amino acid sequence, an exchange from isoleucine (I) to valine (V) occurred. Expression of the protease variant occurred in a manner usual in the art, by transforming *Bacillus subtilis* DB 104 (Kawamura and Doi (1984), J. Bacteriol., Vol. 160 (1), pp. 442-444) with a corresponding expression vector and subsequent culturing of the transformands expressing the protease variant.

Example 2

Ascertaining Cleaning Performance when Used in a Commercially Usual Powdered Washing Agent Standardized stained textiles were used for this Example. The following stain and textiles were used:

grass on cotton: product no. 164 obtainable from Eidgenössische Material-und Prüanstalt (EMPA) Testmaterialen AG, St. Gallen, Switzerland, whole egg/pigment (whole egg/carbon black) on cotton: product no. 10N of wfk Testgewebe GmbH [Test fabrics], Brüggen-Bracht, Germany, chocolate milk/carbon black on cotton: product no. C-03 obtainable from CFT (Center For Testmaterials) B.V., Vlaardingen, Netherlands, cocoa on cotton: product no. 112 obtainable from Eidgenössische Material-und Prüanstalt (EMPA) Testmaterialen AG, St. Gallen, Switzerland, blood-milk/ink on cotton: product no. C-05 obtainable from CFT (Center For Testmaterials) B.V., Vlaardingen, Netherlands.

Using this test material, a variety of washing-agent formulations were investigated in terms of their cleaning performance. For this, the batches were washed for 60 minutes at a temperature of 40° C. The dosing ratio was 5.9 g of washing agent per liter of washing bath. Washing was performed with tap water having a hardness of 16 degrees of German hardness.

A baseline washing-agent formulation of the following composition was used as a control washing agent (all indications in percent by weight): 10% linear alkylbenzenesulfonate (sodium salt), 1.5% C12 to C18 fatty alcohol sulfate (sodium salt), 2.0% C12 to C18 fatty alcohol with 7 EO, 20% sodium carbonate, 6.5% sodium hydrogen carbonate, 4.0% amorphous sodium disilicate, 17% sodium carbonate peroxohydrate, 4.0% TAED, 3.0% polyacrylate, 1.0% carboxymethyl cellulose, 1.0% phosphonate, 25% sodium sulfate, remainder: foam inhibitors, optical brighteners, scents. The baseline washing-agent formulation had the following proteases added to it, on an equal-activity basis (5 PU/ml final concentration), for the various series of experiments: protease variant according to the present invention having an amino acid sequence I21V in accordance with SEQ ID NO. 1 (hence corresponding to SEQ ID NO. 2, hereinafter referred to as Batch 1), and a corresponding control protease in accordance with SEQ ID NO. 1 that does not exhibit the amino acid substitution I21V (Batch 2).

After washing, the whiteness of the washed textiles was measured. The measurement was carried out on a Minolta CM508d spectrometer (D65 illumination, 10°). The unit had previously been calibrated using a white standard provided with the unit. The results obtained are the difference in reflectance values between a washing operation using a washing agent containing a protease, and a concurrently performed control washing operation using a washing agent having no protease. "STDEV" indicates the standard deviation for experimental batches carried out concurrently. The results are summarized in Table 1 below and allow an immediate conclusion as to the contribution made by the particular contained enzyme to the cleaning performance of the agent being used.

TABLE 1

Washing results with a powdered washing agent at 40° C.

| Stain | Batch 1 | STDEV | Batch 2 | STDEV |
|---|---|---|---|---|
| A | 4.8 | 0.7 | 3.0 | 0.2 |
| B | 7.4 | 0.7 | 6.9 | 0.4 |
| C | 11.1 | 0.9 | 8.6 | 0.6 |
| D | 5.6 | 0.2 | 2.0 | 0.5 |
| E | 13.3 | 1.6 | 11.4 | 0.6 |

It is evident that the protease as contemplated herein exhibits better cleaning performance as compared with the control. The protease as contemplated herein furthermore exhibits very good cleaning performance effects in particular on chocolate- or cocoa-containing stains.

---

The invention claimed is:

1. A protein comprising a protease that is at least 91.5% identical to the amino acid sequence indicated in SEQ ID NO. 1 over its entire length, and exhibits the amino acid substitution I21V in the count in accordance with SEQ ID NO. 1.

2. A washing or cleaning agent comprising:
a protein comprising a protease that is at least 91.5% identical to the amino acid sequence indicated in SEQ ID NO. 1 over its entire length, and exhibits the amino acid substitution I21V in the count in accordance with SEQ ID NO. 1.

3. The washing or cleaning agent according to claim 2, wherein the washing or cleaning agent is:

(a) present in solid form as a pourable powder having a bulk weight from about 300 g/l to about 1200 g/l;
(b) present in pasty or in liquid form;
(c) present as a one-component system; or
(d) distributed into multiple components.

4. The washing or cleaning agent of claim 2, wherein the protease is present in an amount of from about 2 μg to about 20 mg of the washing or cleaning agent.

5. The washing or cleaning agent of claim 2, wherein the protease is encased with a substance that is impermeable to the protease at room temperature or in the absence of water.

* * * * *

SEQUENCE LISTING

```
<160> NUMBER OF SEQ ID NOS: 4

<210> SEQ ID NO 1
<211> LENGTH: 269
<212> TYPE: PRT
<213> ORGANISM: Bacillus sp.

<400> SEQUENCE: 1

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140
```

```
Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
                260                 265

<210> SEQ ID NO 2
<211> LENGTH: 269
<212> TYPE: PRT
<213> ORGANISM: Bacillus sp.

<400> SEQUENCE: 2

Gln Gln Thr Val Pro Trp Gly Ile Thr Arg Val Gln Ala Pro Thr Val
1               5                   10                  15

His Asn Arg Gly Val Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
        50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255
```

Phe Gly Ser Gly Leu Val Asn Ala Asp Ala Ala Thr Arg
            260                 265

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 4
<211> LENGTH: 810
<212> TYPE: DNA
<213> ORGANISM: Bacillus sp.

<400> SEQUENCE: 4
caacaaaccg ttccatgggg tattacacgt gtacaagctc ccactgtgca taatcgtgga      60
gtaacaggat ctggagttaa agtcgctata cttgatacag gtatagctca gcatagtgat     120
ttaaccattc gtgggggagc aagctttgta ccaggagagt caacaacggc tgatctaaat     180
ggtcatggta ctcacgttgc tggaacagtg gccgctctta ataattcaat tggtgtgatc     240

-continued

```
ggtgtggcac caagtgctga cctatacgct gtaaaggtat taggagcaaa tggtagagga    300
agcgtgagtg ggattgctca aggtctagag tgggctgcaa cgaataacat gcatattgca    360
aacatgagtc tcggtagtga tgcacctagc actacattag agcgtgcagt taactatgcg    420
acaagccgtg gagttctcgt cattgcggct actggtaaca atggtactgg ttccattggc    480
tacccagctc gttatgcaaa cgcaatggct gtaggagcga ctgaccaaaa caacagacgt    540
gcgagctttt ctcaatatgg cacaggaatt gatattgttg cacctggtgt tggaattcaa    600
agcacatacc taaataatag ctatgctagt atgcctggaa catcaatggc tacacctcat    660
gttgctggag tagctgcgct tgttaaacaa aaaaatccat cttggaatgc gactcaaatt    720
cgtaatcatt tgaaaaatac tgcgacgaat ctaggaaact catctcaatt tggtagtgga    780
ctagttaatg cagatgcagc aacgcgctaa                                    810
```